United States Patent
Küsters et al.

(10) Patent No.: US 8,178,566 B2
(45) Date of Patent: May 15, 2012

(54) CRYSTAL FORM OF EPOTHILONE B AND USE IN PHARMACEUTICAL COMPOSITIONS

(75) Inventors: Ernst Küsters, Eschbach (DE); Michael Mutz, Freiburg (DE); Frank Stowasser, Murg (DE)

(73) Assignee: Novartis AG, Basel (CH)

( * ) Notice: Subject to any disclaimer, the term of this patent is extended or adjusted under 35 U.S.C. 154(b) by 510 days.

(21) Appl. No.: 12/376,973

(22) PCT Filed: Aug. 14, 2007

(86) PCT No.: PCT/EP2007/007173
§ 371 (c)(1),
(2), (4) Date: Feb. 10, 2009

(87) PCT Pub. No.: WO2008/019820
PCT Pub. Date: Feb. 21, 2008

(65) Prior Publication Data
US 2010/0160393 A1     Jun. 24, 2010

(30) Foreign Application Priority Data
Aug. 16, 2006   (EP) ..................................... 06119043

(51) Int. Cl.
*A61K 31/425* (2006.01)
*A61K 31/33* (2006.01)
*C07D 277/30* (2006.01)

(52) U.S. Cl. ........................................ 514/365; 548/204

(58) Field of Classification Search ................. 514/366, 514/183, 166; 548/204
See application file for complete search history.

(56) References Cited

FOREIGN PATENT DOCUMENTS

| | | |
|---|---|---|
| EP | 1428826 | 6/2004 |
| WO | WO 99/39694 | 8/1999 |
| WO | 02/14323 | 2/2002 |
| WO | WO 02/46196 | 6/2002 |

*Primary Examiner* — Raymond Henley, III
(74) *Attorney, Agent, or Firm* — George R. Dohmann

(57) ABSTRACT

The invention relates to new crystal forms of epothilone B.

5 Claims, No Drawings

CRYSTAL FORM OF EPOTHILONE B AND USE IN PHARMACEUTICAL COMPOSITIONS

This is a National Stage of International Application No. PCT/EP2007/007173 filed 14 Aug. 2007, the entire disclosure of which is hereby incorporated by reference.

The invention relates to new crystal forms of epothilones, especially epothilone B, their usage in the production of pharmaceutical preparations, new pharmaceutical preparations comprising these new crystal forms and/or the use of these compounds in the treatment of proliferative diseases such as tumours, or in the production of pharmaceutical formulations which are suitable for this treatment.

BACKGROUND TO THE INVENTION

Of the existing cytotoxic active ingredients for treating tumours, Taxol® (Paclitaxel; Bristol-Myers Squibb), a microtubuli-stabilising agent, plays an important role and has remarkable commercial success. However, Taxol has a number of disadvantages. In particular, its very poor solubility in water is a problem. It therefore became necessary to administer Taxol® in a formulation with Cremophor EL® (polyoxyethylated castor oil; BASF, Ludwigshafen, Germany). Cremophor EL® has severe side effects; for example it causes allergies which in at least one case have led even to the death of a patient.

Although the Taxan class of microtubuli-stabilising anticancer agents has been commended as "perhaps the most important addition to the pharmaceutical armory against cancer in the last decade" (see Rowinsky E. K., Ann. rev. Med. 48, 353-374 (1997)), and despite the commercial success of Taxol®, these compounds still do not appear to represent a really great breakthrough in the chemotherapy of cancer. Treatment with Taxol® is linked with a series of significant side effects, and a few primary classes of compact tumours, namely colon and prostate tumours, respond to this compound only to a small extent (see Rowinsky E. K., inter alia). In addition, the efficacy of Taxol can be impaired and even completely neutralised by acquired resistance mechanisms, especially those based on the overexpression of phosphoproteins, which act as efflux pumps for active ingredients, such as "Multidrug Resistance" due to overexpression of the multidrug transport glycoprotein "P-glycoprotein".

Epothilones A and B represent a new class of microtubuli-stabilising cytotoxic active ingredients (see Gerth, K. et al., J. Antibiot. 49, 560-3 (1966)) of the formulae:

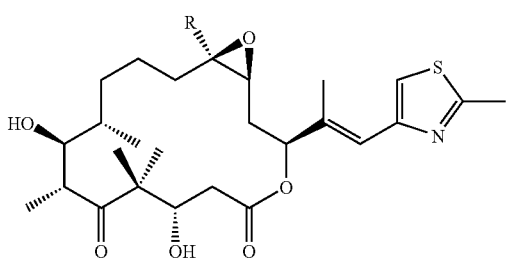

wherein R signifies hydrogen (epothilone A) or methyl (epothilone B).

These compounds have the following advantages over Taxol®:
a) They have better water-solubility and are thus more easily accessible for formulations.
b) It has been reported that, in cell culture experiments, they are also active against the proliferation of cells, which, owing to the activity of the P-glycoprotein efflux pump making them "multidrug resistant", show resistance to treatment with other chemotherapy agents including Taxol® (see Bolag, D. M., et al., "Epothilones, a new class of microtubuli-stabilizing agents with a Taxol-like mechanism of action", Cancer Research 55, 2325-33 (1995)). And
c) it could be shown that they are still very effective in vitro against a Taxol®-resistant ovarian carcinoma cell line with modified β-tubulin (see Kowalski, R. J., et al., J. Biol. Chem. 272(4), 2534-2541 (1997)).

Pharmaceutical application of the epothilones, for example for tumour treatment, is possible in an analogous manner to that described for Taxol, see for example U.S. Pat. No. 5,641,803; U.S. Pat. No. 5,496,804; U.S. Pat. No. 5,565,478).

Epothilones may be produced as described in patent application WO 93/10121, U.S. Pat. No. 6,194,181, WO 98/25929, WO 98/08849, WO 99/43653, WO 98/22461 and WO 00/31247 in each case in particular in the compound claims and the final products of the working examples, the subject-matter of the final products, the pharmaceutical preparations and the claims is hereby incorporated into the present application by reference to this publications. Epothilone derivatives of formula I, especially epothilone B, can be administered as part of pharmaceutical compositions which are disclosed in WO 99/39694.

DETAILED DESCRIPTION OF THE INVENTION

In one aspect the invention relates to new crystal forms of epothilone B.

The general terms used hereinabove and hereinbelow preferably have the meanings given hereinbelow:

Where reference is made hereinabove and hereinbelow to documents, these are incorporated insofar as is necessary.

The prefix "lower" always indicates that the correspondingly named radical contains preferably up to a maximum of 7 carbon atoms, in particular up to 4 carbon atoms, and is branched or unbranched. Lower alkyl may be for example unbranched or branched once or more, and is e.g. methyl, ethyl, propyl such as isopropyl or n-propyl, butyl such as isobutyl, sec.-butyl, tert.-butyl or n-butyl, or also pentyl such as amyl or n-pentyl.

Epothilones are primarily epothilone A and/or B, but also other epothilones, for example epothilones C and D named in International Application WO 97/19086 and WO 98/22461, epothilones E and F named in WO 98/22461, and further epothilones obtainable from corresponding microorganisms.

PREFERRED EMBODIMENT OF THE INVENTION

The invention relates to new crystal forms of epothilone B, especially a crystal form of epothilone B described as modification C.

The crystal forms can be distinguished in particular by their X-ray diagrams. X-ray diagrams taken with a diffractometer and using Cu—K$\alpha_1$-radiation are preferably used to characterize solids of organic compounds. X-ray diffraction diagrams are used particularly successfully to determine the crystal modification of a substance. To characterize the existing crystal modification C of epothilone B, the measurements are made at an angle range (2θ) of 2° and 35° with samples of substance that are kept at room temperature.

Single Crystal Structure of Modification C

Modification C is characterized by an orthorhombic space group P2₁2₁2₁. The lattice parameters (at 100 K) are:

Structural Data of Modification C
Crystallized from isopropylacetate

| | |
|---|---|
| A (Å) | 10.3302(2) |
| b (Å) | 12.0132(14) |
| c (Å) | 27.070(4) |
| Beta (°) | |
| Cell volume (Å3) | 3359.4(7) |
| Z | 4 |
| Density (g/cm3) | 1.206 |
| Solvent EPO906: | 1:1 |

The X-ray diffraction diagram thus determined (reflection lines and intensities of the most important lines) from crystal modification C (modification C) of epothilone B is characterized by the following table.

| 2θ | Intensity |
|---|---|
| 6.5 | medium |
| 11.8 | medium |
| 13.1 | medium |
| 17.5 | strong |
| 18.3 | strong |
| 19.6 | medium |
| 21.6 | medium |

The new crystal form is especially stable, and they are therefore suitable as active ingredients for solid forms of administration, for storing in solid form or as intermediates (with particularly good storability) in the preparation of solid or liquid forms of administration.

The invention also relates to the use of the new crystal form, referred to hereinafter as active ingredient) in the production of pharmaceutical preparations, new pharmaceutical preparations which contain these new crystal forms, and/or the use of these compounds in the treatment of proliferative diseases, such as tumours. In the following, where pharmaceutical preparations or compositions which comprise or contain the active ingredient are mentioned, in the case of liquid compositions or compositions which no longer contain the crystal form as such, this is always understood to mean also the pharmaceutical preparations obtainable using the crystal forms (for example infusion solutions obtained using crystal form C of epothilone B), even if they no longer contain the respective crystal form (for example because they exist in solution).

The invention also relates especially to the use of a new crystal form of epothilone B, in the production of pharmaceutical preparations, characterised by mixing a new crystal form of epothilone B with one or more carriers.

The invention also relates to a method of treating warm-blooded animals suffering from a proliferative disease, characterised by administering a dose of epothilone B which is effective for treating said disease in one or the new crystal forms to a warm-blooded animal requiring such treatment, also including in particular the treatment with those preparations that are produced using one of the new crystal forms.

To produce the pharmaceutical preparations, the active ingredient may be used for example in such a way that the pharmaceutical preparations contain an effective amount of the active ingredient together or in a mixture with a significant amount of one or more organic or inorganic, liquid or solid, pharmaceutically acceptable carriers.

The invention also relates to a pharmaceutical composition which is suitable for administration to a warm-blooded animal, especially humans, in the treatment of a proliferative disease, such as a tumour, the composition containing an amount of active ingredient that is suitable for treating said disease, together with a pharmaceutically acceptable carrier.

The pharmaceutical compositions according to the invention are those intended for enteral, especially nasal, rectal or oral, or preferably parenteral, especially intramuscular or intravenous administration to warm-blooded animals, especially humans, and they contain an effective dose of the active ingredient on its own or together with a significant amount of a pharmaceutically acceptable carrier. The dose of the active ingredient is dependent on the type of warm-blooded animal, the body weight, the age and the individual condition, individual pharmacokinetic situations, the disease to be treated and the type of administration.

The pharmaceutical compositions contain ca. 0.0001% to ca. 95%, preferably 0.001% to 10% or 20% to ca. 90% of active ingredient. Pharmaceutical compositions according to the invention may be present for example in unit dose forms, such as in the form of ampoules, vials, suppositories, dragées, tablets or capsules.

The pharmaceutical compositions according to the present invention are produced by known processes, for example by conventional dissolving, lyophilizing, mixing, granulating or manufacturing processes.

Solutions of the active ingredient, also suspensions, and in particular aqueous solutions or suspensions, are preferably employed, whereby it is also possible, for example in the case of lyophilised compositions which contain the active ingredient on its own or together with a pharmaceutically acceptable carrier, for example mannitol, for the solutions or suspensions to be prepared prior to administration. The pharmaceutical compositions may be sterilised and/or may contain excipients, for example preservatives, stabilisers, moisture-retaining agents and/or emulsion-forming agents, dissolving aids, salts for regulating osmotic pressure and/or buffers, and they are produced by known processes, for example by conventional dissolving or lyophilising processes. The solutions or suspensions mentioned may comprise viscosity-increasing substances, such as sodium carboxymethylcellulose, carboxymethylcellulose, dextran, polyvinylpyrrolidone or gelatin.

Suspensions in oil contain as the oil component vegetable oils, synthetic oils or semi-synthetic oils, which are customary for injection purposes. Notable examples are in particular liquid fatty acid esters, which contain as the acid component a long-chained fatty acid with 8 to 22, especially 12 to 22, carbon atoms, for example lauric acid, tridecylic acid, myristic acid, pentadecylic acid, palmitic acid, margaric acid, stearic acid, arachidic acid, behenic acid or corresponding unsaturated acids, for example oleic acid, elaidic acid, erucic acid, brassidic acid or linoleic acid, if desired with the addition of antioxidants, for example vitamin E, β-carotene or 3,5-di-tert-butyl-4-hydroxytoluene. The alcoholic component of these fatty acid esters preferably has a maximum of 6 carbon atoms and is a mono- or polyhydroxy alcohol, for example a mono-, di- or tri-hydroxy alcohol, for example methanol, ethanol, propanol, butanol or pentanol, or an isomer thereof, but especially glycol and glycerol. The following examples of fatty acid esters may be mentioned in particular: propyl myristate, isopropyl palmitate, "Labrafil M 2375" (polyoxyethylene glycerol trioleate, Gattefossé, Paris), "Miglyol 812" (triglyceride of saturated fatty acids having a chain length of 8 to 12 carbon atoms, Hüls AG, Germany), but in particular vegetable oils such as cottonseed oil, almond oil, olive oil, castor oil, sesame oil, soybean oil and in particular peanut oil.

The injection or infusion preparations are produced according to customary methods under sterile conditions; the same applies also to the filling of the compositions into ampoules or vials and sealed containers.

Preference is given to an infusion solution which contains the active ingredient and a pharmaceutically acceptable organic solvent.

The pharmaceutically acceptable organic solvents which may be used in a formulation according to the invention can be selected from all such solvents which are familiar to a person skilled in the art. The solvent is preferably selected from an alcohol, e.g. absolute ethanol, ethanol/water mixtures, preferably 70% ethanol, polyethylene glycol 300, polyethylene glycol 400, polypropylene glycol and N-methylpyrrolidone, especially polypropylene glycol or 70% ethanol.

Particular preference is given to a formulation in pure polyethylene glycol, which is diluted prior to infusion in an appropriate solution, such as physiological saline.

The active ingredient is present in the formulation in a concentration of 0.001 to 100 mg/ml, preferably from ca. 0.05 to 5 mg/ml, or from 5 to 50 mg/ml.

Formulations of this type are easily stored as vials or ampoules. The vials or ampoules are typically made of glass, e.g. boron silicate. The vials or ampoules may be appropriate for any volume which is known from the prior art. They are preferably of sufficient size to be able to accept 0.5 to 5 ml of the formulation.

Prior to administration, the formulations have to be diluted in an aqueous medium suitable for intravenous administration before the active ingredient can be administered to patients.

It is preferable for the infusion solution to have the same or basically the same osmotic pressure as body fluids. Consequently, the aqueous medium contains an isotonic agent which has the effect of rendering the osmotic pressure of the infusion solution the same or basically the same as the osmotic pressure of body fluids.

The isotonic agent can be selected from all agents that are familiar to a person skilled in the art, for example mannitol, dextrose, glucose and sodium chloride. The isotonic agent is preferably glucose or sodium chloride. The isotonic agents may be used in quantities which impart the same or basically the same osmotic pressure to the infusion solution as body fluids. The exact quantities required can be determined by routine experiments and depend on the composition of the infusion solution and the type of isotonic agent.

The concentration of isotonizing agent in the aqueous medium depends on the type of each agent used. If glucose is used, it is preferably used in a concentration of 1 to 5% w/v, preferably 5% w/v. If the isotonizing agent is sodium chloride, it is preferably used in quantities of up to 1%, preferably ca. 0.9% w/v.

The infusion solution can be diluted with the aqueous medium. The amount of aqueous medium used is chosen according to the desired concentration of active ingredient in the infusion solution. The infusion solution is preferably produced by mixing a vial or an ampoule containing the infusion concentrate (see above) with an aqueous medium, so that a volume of between 200 ml and 1000 ml is attained with the aqueous medium. Infusion solutions may contain other additives that are normally used in formulations for intravenous administration. These additives also include antioxidants.

Antioxidants may be used to protect the active ingredient from degradation by oxidation. Antioxidants may be selected from those which are familiar to the person skilled in the art and which are suitable for intravenous formulations. The amount of antioxidant can be determined by routine experiments. As an alternative to adding an antioxidant, or additionally thereto, the antioxidant effect can be achieved by restricting the oxygen (air) contact with the infusion solution. This can be achieved in a simple way, by treating the vessel containing the infusion solution with an inert gas, e.g. nitrogen or argon.

Infusion solutions can be produced by mixing an ampoule or a vial with the aqueous medium, e.g. a 5% glucose solution in WFI in an appropriate container, e.g. an infusion bag or an infusion bottle.

Containers for the infusion solutions may be selected from conventional containers that are non-reactive with the infusion solution. Among those suitable are glass containers, especially of boron silicate, but plastic containers such as plastic infusion bags, are preferred.

Plastic containers may also be made of thermoplastic polymers. The plastic materials may also contain additives, e.g. softeners, fillers, antioxidants, antistatic agents or other customary additives.

Suitable plastics for the present invention should be resistant to elevated temperatures used for sterilisation. Preferred plastic infusion bags are the PVC materials which are known to the person skilled in the art.

A large range of container sizes may be considered. When selecting the size of the container, the factors to be taken into consideration are especially the solubility of epothilones in an aqueous medium, easy handling, and if appropriate, storage of the container. It is preferable to use containers which hold between ca. 200 and 1000 ml of infusion solution.

Owing to their good formulating properties, the new crystal forms of epothilone B according to the invention are especially suitable for the simple and reproducible production of the said infusion solutions. However, the new crystal forms are especially suitable for the production of pharmaceutical formulations which contain the active ingredient in solid form, for example oral formulations.

Pharmaceutical formulations for oral application may be obtained by combining the active ingredient with solid carriers, if desired by granulating the resultant mixture, and further processing the mixture, if desired or if necessary, after adding suitable adjuvants, into tablets, dragée cores or capsules. It is also possible to embed them in plastic substrates which enable the active ingredient to be diffused or released in measured quantities.

Suitable pharmaceutically employable carriers are especially fillers, such as lactose, saccharose, mannitol or sorbitol, cellulose preparations, and/or calcium phosphates, for example tricalcium phosphate or calcium hydrogen phosphate, and binders, such as starches, for example maize, wheat, rice or potato starch, gelatin, tragacanth, methyl cellulose, hydroxypropyl methyl cellulose, sodium carboxymethylcellulose, and/or polyvinyl pyrrolidone, and/or, if desired, disintegrators, such as the above-mentioned starches, crosslinked vinylpyrrolidones, agar, alginic acid or a salt thereof, such as sodium alginate. Adjuvants are in particular flow-improving agents and lubricants, e.g. silicates, talcum, stearic acid or salts thereof, such as magnesium or calcium stearate and/or polyethylene glycol. Dragée cores are provided, if desired, with appropriate gastric-juice-resistant coatings, using inter alia concentrated sugar solutions, gum arabic, talcum, polyvinyl pyrrolidone, polyethylene glycol and/or titanium dioxide, or coating solutions in suitable organic solvents, or in order to produce gastric-juice-resistant coatings, solutions of appropriate cellulose preparations, such as ethyl cellulose phthalate or hydroxypropyl methyl cellulose phthalate. Capsules are dry capsules consisting of gelatin or pectin, and if required, a softener such as glycerol or sorbitol. The dry capsules may contain the active ingredient in the form of granules, for example with fillers, such as lactose, binders, such as starches, and/or lubricants, such as talc or magnesium stearate, and where appropriate stabilizers. In soft capsules, the active ingredient may be present in dissolved or preferably suspended form, whereby oily adjuvants such as fat oils, paraffin oil or liquid propylene glycols are added; stabilizers and/or antibacterial additives may also be added. Dyes or pigments can be added to the tablets or dragée coatings, for example to improve identification or to distinguish different dosages of active ingredient.

The usage in the treatment of a proliferative disease with one of the crystal forms B and in particular A preferably takes place whereby the crystal form (preferably as for the usage in the preparation of an infusion solution, as described above) is administered to a warm-blooded animal, especially a human, in a dose which can be determined at between 20 and 133%, preferably between 25 and 100%, of the Maximum Tolerated Dose (MTD) by standard methods, for example using a modified Fibronacci series, in which the increases in dosages for successive amounts are 100%, 67%, 50% and 40% followed by 33% for all subsequent doses; and, if necessary, one or more further doses administered in the dosage range given above for the first dose, each dose after a period of time which allows sufficient recovery of the individual being treated after the preceding administration, in particular one week or more after the first administration, preferably 2 to 10 weeks, especially 3 to 6 weeks after each preceding administration. In general, this treatment scheme, in which a high dosage is administered once, twice or several times with sufficiently long intervals between the individual administrations for recovery to take place, is preferred over a more frequent treatment with lower doses, since hospitalisation is less frequent and for a shorter period and an improved anti-tumour effect can be expected. The dosage of epothilone B for humans is preferably between 0.1 and 50 mg/m$^2$, preferably between 0.2 and 10 mg/m$^2$.

The following Examples serve to illustrate the invention without limiting its scope.

Caution: When handling epothilones, appropriate protective measures must be taken, where necessary, in view of their high toxicity.

Example 1

Crystal Modification C of Epothilone B 20 mg of epothilone B are dissolved in an excess, 5 ml, of isopropyl acetate. By slow evaporation at room conditions (25° C.) needle like single crystals are obtained after 2 days. The product is filtered and dried. The crystal modification C of epothilone B is obtained.

Example 2

Infusion Concentrate

By dissolving in polyethylene glycol PEG 300, crystal modification C of epothilone B, is produced in a preconcentrate to produce infusion solutions, and stored in vials.

What is claimed is:

1. A crystal form of epothilone B, which is characterised by the X-ray diffraction diagram reproduced in the form of a table;

| 2θ | Intensity |
|---|---|
| 17.5 | strong |
| 18.3 | strong. |

2. A crystal form of epothilone B, which is characterised by the X-ray diffraction diagram reproduced in the form of a table;

| 2θ | Intensity |
|---|---|
| 6.5 | medium |
| 11.8 | medium |
| 13.1 | medium |
| 17.5 | strong |
| 18.3 | strong |
| 19.6 | medium |
| 21.6 | medium. |

3. A crystal form of epothilone B, which is characterised by the Structural data when crystallized from isopropylacetate

| | |
|---|---|
| A (Å) | 10.3302(2) |
| b (Å) | 12.0132(14) |
| c (Å) | 27.070(4) |
| Beta (°) | — |
| Cell volume (Å3) | 3359.4(7) |
| Z | 4 |
| Density (g/cm3) | 1.206 |
| Solvent:EPO906 | 1:1. |

4. A pharmaceutical composition which is suitable for administration to a warm-blooded animal for the treatment of a proliferative disease, which contains a quantity of an active ingredient according to claim 1, which is suitable for the treatment of said disease together with a pharmaceutically acceptable carrier.

5. A method of treating a warm-blooded animal suffering from a proliferative disease in need thereof, which comprises administering a therapeutically effective dose-dosage of the crystal form of epothilone B according to claim 1 to the warm-blooded animal requiring such treatment.

* * * * *